United States Patent
Taylor et al.

(10) Patent No.: US 9,662,174 B2
(45) Date of Patent: May 30, 2017

(54) MICRO-FORCE GUIDED COOPERATIVE CONTROL FOR SURGICAL MANIPULATION OF DELICATE TISSUE

(75) Inventors: Russell H. Taylor, Severna Park, MD (US); Marcin Arkadiusz Balicki, Baltimore, MD (US); James Tahara Handa, Baltimore, MD (US); Peter Louis Gehlbach, Hunt Valley, MD (US); Iulian Iordachita, Towson, MD (US); Ali Uneri, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 349 days.

(21) Appl. No.: 13/813,738

(22) PCT Filed: Aug. 2, 2011

(86) PCT No.: PCT/US2011/046278
§ 371 (c)(1),
(2), (4) Date: Jul. 22, 2013

(87) PCT Pub. No.: WO2012/018823
PCT Pub. Date: Feb. 9, 2012

(65) Prior Publication Data
US 2013/0304258 A1    Nov. 14, 2013

Related U.S. Application Data
(60) Provisional application No. 61/370,032, filed on Aug. 2, 2010.

(51) Int. Cl.
*A61F 9/007* (2006.01)
*B25J 9/16* (2006.01)
(Continued)

(52) U.S. Cl.
CPC .......... *A61B 19/2203* (2013.01); *A61B 34/30* (2016.02); *A61B 34/72* (2016.02);
(Continued)

(58) Field of Classification Search
CPC ........ A61B 19/2203; A61B 2019/2211; A61B 2019/2223; A61B 2019/2296;
(Continued)

(56) References Cited

U.S. PATENT DOCUMENTS 5,231,693 A * 7/1993 Backes .................. B25J 9/1661
                                                        318/568.1
5,572,999 A    11/1996 Funda et al.
(Continued)

FOREIGN PATENT DOCUMENTS

CN         101390027 A       3/2009
WO      WO-02/060653 A2     8/2002
(Continued)

OTHER PUBLICATIONS

Kumar et al.; "Preliminary experiments in cooperative human/robot force control for robot assisted microsurgical manipulation"; Robotics and Automation, 2000; Proceedings. ICRA '00. IEEE International Conference on; vol. 1; pp. 610-617.*
(Continued)

*Primary Examiner* — Stephen Holwerda
(74) *Attorney, Agent, or Firm* — Venable LLP; Henry J. Daley; Laura G. Remus

(57) ABSTRACT

A method and system for micro-force guided cooperative control that assists the operator in manipulating tissue in the direction of least resistance. A tool holder receives a surgical tool adapted to be held by a robot and a surgeon. A first sensor measures interaction forces between a tip of the surgical tool and tissue of a region of interest. A second sensor measures interaction forces between the surgeon and
(Continued)

a handle to the surgical tool. A data processor is configured to perform an algorithm to actively guide the surgical tool by creating a bias towards a path of least resistance and limit directional tool forces of the surgical tool as a function of handle input forces and tip forces. This function offers assistance to challenging retinal membrane peeling procedures that require a surgeon to delicately delaminate fragile tissue that is susceptible to hemorrhage and tearing due to undesirable forces.

16 Claims, 5 Drawing Sheets

(51) Int. Cl.
    *A61B 19/00*     (2006.01)
    *G05B 19/423*     (2006.01)
    *A61B 34/30*     (2016.01)
    *A61B 34/00*     (2016.01)
    *A61B 90/00*     (2016.01)

(52) U.S. Cl.
    CPC .......... *B25J 9/1689* (2013.01); *G05B 19/423* (2013.01); *A61B 2090/064* (2016.02); *A61B 2090/065* (2016.02); *A61F 9/007* (2013.01); *G05B 2219/36432* (2013.01); *G05B 2219/40064* (2013.01); *G05B 2219/45123* (2013.01); *Y10S 901/46* (2013.01)

(58) Field of Classification Search
    CPC ...... A61B 2019/2249; A61B 2019/465; A61B 2019/464; B25J 9/1689; B25J 9/1692; B25J 9/1694; A61F 9/007; G05B 19/423; G05B 2219/36432; G05B 2219/40064; G05B 2219/45123; Y10S 901/46
    USPC ................ 700/245, 250, 260, 261, 262, 264
    See application file for complete search history.

(56) References Cited

U.S. PATENT DOCUMENTS

| | | | |
|---|---|---|---|
| 5,831,408 A * | 11/1998 | Jacobus ................. | B25J 9/1689 318/568.1 |
| 6,084,371 A * | 7/2000 | Kress ..................... | B25J 9/1689 318/566 |
| 6,246,200 B1 | 6/2001 | Blumenkranz et al. | |
| 6,424,885 B1 * | 7/2002 | Niemeyer .............. | A61B 34/70 600/109 |
| 2002/0032452 A1 | 3/2002 | Tierney et al. | |
| 2002/0120188 A1 * | 8/2002 | Brock ................... | A61B 5/7455 600/407 |
| 2004/0163497 A1 * | 8/2004 | Ormachea .............. | B23P 19/04 81/57.4 |
| 2010/0114288 A1 * | 5/2010 | Haller ................ | A61B 17/3468 607/137 |
| 2011/0125165 A1 | 5/2011 | Simaan et al. | |

FOREIGN PATENT DOCUMENTS

WO    WO-2007/096322 A2    8/2007
WO    WO-2009/140688 A2    11/2009

OTHER PUBLICATIONS

Kang et al.; "Autonomous suturing using minimally invasive surgical robots"; Control Applications, 2000; Proceedings of the 2000 IEEE International Conference on; pp. 742-747.*

Bloom et al.; "Advanced technology in surgery"; Current Problems in Surgery; vol. 39, issue 8; Aug. 2002; pp. 745-830.*
Yen et al.; "Intelligent human-machine cooperative robot for orthopaedic surgery"; Circuits and Systems, 2008; APCCAS 2008; IEEE Asia Pacific Conference on; pp. 741-744.*
Bloom; "Advanced technology in surgery"; Current Problems in Surgery; vol. 39, issue 8; Aug. 2002; pp. 745-830.*
Berkelman et al., "A miniature microsurgical instrument tip force sensor for enhanced force feedback during robot-assisted manipulation," IEEE Transactions on Robotics and Automation, vol. 19., No. 5, 2003, pp. 917-922.
Kazanzides et al., "Force Sensing and Control for a Surgical Robot," Proceedings of the 1992 IEEE International Conference on Robotics and Automation, 1992, pp. 612-617.
Kumar et al., "Preliminary experiments in cooperative human robot force control for robot assisted microsurgical manipulation," Proceedings of the 2000 IEEE International Conference on Robotics and Automation, 2000, pp. 610-617.
Mitchell et a., "Development and Application of a New Steady-Hand Manipulator for Retinal Surgery," IEEE International Conference on Robotics and Automation, 2007, pp. 623-629.
Taylor et al., "A Steady-Hand Robotic System for Microsurgical Augmentation," International Journal of Robotics Research, vol. 19., No. 12, pp. 1201-1210.
Uneri et al., "New steady-hand Eye Robot with micro-force sensing for vitreoretinal surgery," In: Proceedings of IEEE BioRob, pp. 814-819, Sep. 26-29, 2010.
Berkelman et al., "Performance evaluation of a cooperative manipulation microsurgical assistant robot applied to stapedotomy," in *MICCAI*. London, UK: Springer-Verlag, 2001, pp. 1426-1429.
Fleming et al., "Cooperative robot assistant for retinal microsurgery," *MICCAI*, pp. 543-550, 2008.
Gentleman et al., "Mechanical characterization of collagen fibers and scaffolds for tissue engineering," *Biomaterials*, vol. 24, No. 21, pp. 3805-3813, 2003.
Gupta et al., "Surgical forces and tactile perception during retinal microsurgery," *Medical Image Computing and Computer-Assisted Intervention (MICCAI)*, pp. 1218-1225, 1999.
Guthart et al., "The intuitive telesurgery system: overview and application," in *IEEE ICRA*, vol. 1, 2000, pp. 618-621.
Iordachita et al., "A sub-millimetric, 0.25 mn resolution fully integrated fiber-optic force-sensing tool for retinal microsurgery," *International Journal of Computer Assisted Radiology and Surgery (IJCARS)*, vol. 4, No. 4, pp. 383-390, Jun. 2009.
Jagtap et al., 'Applied force during vitreoretinal microsurgery with handheld instruments, in *IEEE International Conference on Engineering in Medicine and Biology Society (IEMBS)*, vol. 1, Sep. 2004, pp. 2771-2773.
Nakano et al., "A parallel robot to assist vitreoretinal surgery," *International Journal of Computer Assisted Radiology and Surgery (IJCARS)*, vol. 4, No. 6, pp. 517-26, Nov. 2009.
Riviere et al., "Toward active tremor canceling in handheld microsurgical instruments," *IEEE ICRA*, vol. 19, No. 5, pp. 793-800, Oct. 2003.
Sun et al., "Development and preliminary data of novel integrated optical micro-force sensing tools for retinal microsurgery," in *IEEE ICRA*, May 2009, pp. 1897-1902.
Tan et al., "Design and development of a low-cost flexure-based hand-held mechanism for micromanipulation," in *IEEE ICRA*, May 2009, pp. 4350-4355.
Vagvolgyi et al., "The Surgical Assistant Workstation: a software framework for telesurgical robotics research," in MICCAI Workshop on Systems and Architectures for Computer Assisted Interventions, Midas Journal: http://hdl.handle.net/10380/1466, Sep. 2008.
Wei et al., "Design and theoretical evaluation of micro-surgical manipulators for orbital manipulation and intraocular dexterity," in *IEEE ICRA*, Apr. 2007, pp. 3389-3395.

* cited by examiner (a) CALIBRATION (b) TISSUE

MICRO-FORCE GUIDED COOPERATIVE CONTROL FOR SURGICAL MANIPULATION OF DELICATE TISSUE

CROSS-REFERENCE TO RELATED APPLICATIONS

This application is a 35 U.S.C. §371 U.S. national entry of International Application PCT/US2011/046278 having an international filing date of Aug. 2, 2011, which claims the benefit of U.S. Provisional Application No. 61/370,032 filed on Aug. 2, 2010, the content of each of the aforementioned application is hereby incorporated by reference in their entireties.

STATEMENT OF GOVERNMENTAL INTEREST

This invention was made with U.S. government support under grant no. EB007969 awarded by the National Institutes of Health and EEC9731478 awarded by National Science Foundation. The U.S. government has certain rights in the invention.

FIELD OF THE INVENTION

The present invention pertains to a method and system for cooperative control for surgical tools. More particularly, the present invention pertains to a method and system for micro-guided cooperative control fir surgical manipulation of delicate tissue.

BACKGROUND OF THE INVENTION

Retinal microsurgery is one of the most challenging set of surgical tasks due to human sensory-motor limitations, the need for sophisticated and miniature instrumentation, and the inherent difficulty of performing micron scale motor tasks in a small and fragile environment. In retinal surgery, surgeons are required to perform micron scale maneuvers while safely applying forces to the retinal tissue that are below sensory perception. Surgical performance is further challenged by imprecise instruments, physiological hand tremor, poor visualization, lack of accessibility to some structures, patient movement, and fatigue from prolonged operations. The surgical instruments in retinal surgery are characterized by long, thin shafts (typically 0.5 mm to 0.7 mm in diameter) that are inserted through the sclera (the visible white wall of the eye). The forces exerted by these tools are often far below human sensory thresholds.

The surgeon therefore must rely on visual cues to avoid exerting excessive forces on the retina. These visual cues are a direct result of the forces applied to the tissue, and a trained surgeon reacts to them by retracting the tool and re-grasping the tissue in search of an alternate approach. This interrupts the peeling process, and requires the surgeon to carefully re-approach the target. Sensing the imperceptible microforce cues and preemptively reacting using robotic manipulators has the potential to allow for a continuous peel, increasing task completion time and minimizing the risk of complications. All of these factors contribute to surgical errors and complications that may lead to vision loss.

An example procedure is the peeling of the epiretinal membrane, where a thin membrane is carefully delaminated off the surface of the retina using delicate (20-25 Ga) surgical instruments. The forces exerted on retinal tissue are often far below human sensory thresholds. In current practice, surgeons have only visual cues to rely on to avoid exerting excessive farces, which have been observed to lead to retinal damage and hemorrhage with associated risk of vision loss.

Although robotic assistants such as the DAVINCI™ surgical robotic system have been widely deployed for laparoscopic surgery, systems targeted at microsurgery are still at the research stage. Microsurgical systems include teleoperation systems, freehand active tremor-cancellation systems, and cooperatively controlled hand-over-hand systems, such as the Johns Hopkins "Steady Hand" robots. In steady-hand control, the surgeon and robot both hold the surgical tool; the robot senses forces exerted by the surgeon on the tool handle, and moves to comply, filtering out any tremor. For retinal microsurgery, the tools typically pivot at the sclera insertion point, unless the surgeon wants to move the eyeball. This pivot point may either he enforced by a mechanically constrained remote center-of-motion or software. Interactions between the tool shaft and sclera complicate both the control of the robot and measurement of tool-to-retina forces.

To measure the tool-to-retina forces, an extremely sensitive (0.25 mN resolution) force sensor has been used, which is mounted on the tool shaft, distal to the sclera insertion point. The three sensor allows for measurement of the tool tissue forces while diminishing interference from tool-sclera forces.

In addition, a first-generation steady-hand robot has been specifically designed for vitreoretinal surgery. While this steady-hand robot was successfully used in ex-vivo robot assisted vessel cannulation experiments, it was found to be ergonomically limiting. For example, the first generation steady-hand robot had only a ±30% tool rotation limit. To further expand the tool rotation range, a second generation steady-hand robot has been developed which has increased this range to ±60%. The second generation steady-hand robot utilizes a parallel six-bar mechanism that mechanically provides isocentric motion, without introducing large concurrent joint velocities in the Cartesian stages, which occurred with the first generation steady-hand robots.

The second generation steady-hand robot incorporates both a significantly improved manipulator and an integrated microforce sensing tool, which provides for improved vitreoretinal surgery. However, because of the sensitivity of vitreoretinal surgery, there is still a need in the art for improved control of the tool, to avoid unnecessary complications. For example, complications in vitreoretinal surgery may result from excess and/or incorrect application of forces to ocular tissue. Current practice requires the surgeon to keep operative forces low and safe through slow and steady maneuvering. The surgeon must also rely solely on visual feedback that complicates the problem, as it takes time to detect, assess and then react to the faint cues; a task especially difficult for novice surgeons.

Accordingly, there is a need in the art for an improved control method for surgical tools used in vitreoretinal surgery and the like.

SUMMARY

According to a first aspect of the present invention, a method of cooperative control of a surgical tool, comprising providing a surgical tool to be manipulated during an operation, the surgical tool adapted to be held by a robot and a surgeon, measuring interaction forces between a tip of the surgical tool and tissue of a region of interest, measuring interaction forces between the surgeon and a handle to the surgical tool, actively guiding the surgical tool by creating a bias towards a path of least resistance, and limiting directional tool forces of the surgical tool as a function of handle input forces and tip forces.

According to a second aspect of the present invention, a system for cooperative control of a surgical tool comprises a tool holder for receiving a surgical tool adapted to be held by a robot and a surgeon, a first sensor for measuring interaction forces between a tip of the surgical tool and tissue of a region of interest, a second sensor for measuring interaction forces between the surgeon and a handle to the surgical tool, and a data processor is configured to perform an algorithm to actively guide the surgical tool by creating a bias towards a path of least resistance and limit directional tool forces of the surgical tool as a function of handle input forces and tip forces.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to a novel method and system for micro-force guided cooperative control that assists the operator in manipulating tissue in the direction of least resistance. This function has the potential to aid in challenging retinal membrane peeling procedures that require a surgeon to delicately delaminate fragile tissue that is susceptible to hemorrhage and tearing due to undesirable forces. It can also be useful in other microsurgical tasks such as controlled tearing of tissue in capsularhexis, blunt tissue dissection, or other delicate surgical tasks.

An exemplary embodiment of the invention provides for use of the system and method in cooperatively controlled hand-over-hand systems, such as the robotic assisted surgical system described in "Development and Application of a New Steady-Hand Manipulator for Retinal Surgery", Mitchell et al., IEEE ICRA, pp. 623-629 (2007), and in "New Steady-Hand Eye Robot with Microforce Sensing for Vitreoretinal Surgery Research", A. Uneri, M. Balicki, James Handa, Peter Gehlbach, R. Taylor, and I. Iordachita, International Conference on Biomedical Robotics and Biomechatronics (BIOROB), Tokyo, Sep. 26-29, 2010, pp. 814-819, the entire contents of which are incorporated by reference herein. In steady-hand control, the surgeon and robot both hold the surgical tool. The robot senses forces exerted by the surgeon on the tool handle, and moves to comply, filtering out any tremor. While a specific cooperative control system is described in connection with the above publication, it should be understood that the system and method of the present invention may also be applicable to other cooperatively controlled systems.

Figure 1:
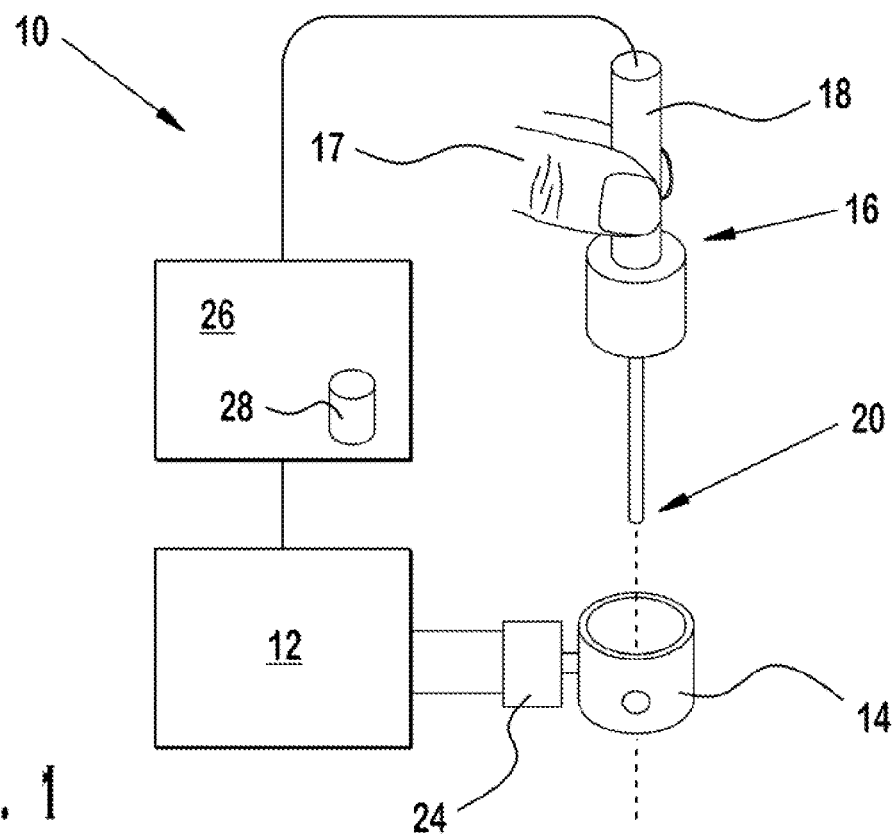
FIG. 1 illustrates a schematic of an exemplary system according to the features of the present invention.
Figure 2:
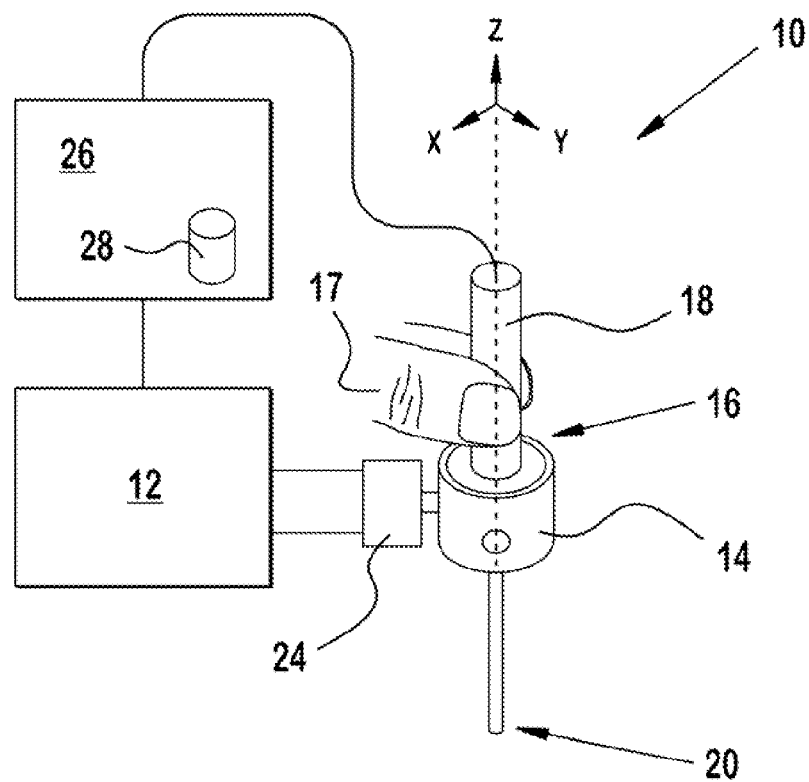
FIG. 2 illustrates a schematic of an exemplary system according to the features of the present invention.

With reference to FIGS. 1 and 2, a first illustrative embodiment of a robotic-assisted surgical system to be used in connection with the present invention is shown. The system 10 may be used in micro-surgery of organs, for example, hollow organs, such as the human eye, but other applications are possible.

As shown in FIGS. 1 and 2, the system 10 includes a tool holder 14 for receiving as surgical tool 16 to be held both a robot 12 and a surgeon 17. The tool holder 14 facilitates the attachment of a variety of surgical tools required during microsurgical procedures, including but not limited to, forceps, needle holder, and scissors. Preferably, the surgeon 17 holds the surgical tool 16 at a tool handle 18, and cooperatively directs the surgical tool 16 with the robot 12 to perform surgery of a region of interest with a tool tip 20. In addition, a force/torque sensor 24 may be mounted at the tool holder 16, which senses forces exerted by the surgeon on the tool, liar use as command inputs to the robot. A number of other sensors known in the art may be used to detect the force between the tool handle 14 and the surgeon 17. Examples include micro-switches, capacitive sensors, optical sensors, force sensors, or pressure sensors on the tool handle 14.

Preferably, a custom mechanical RCM is provided, which improves the stiffness and precision of the robot stages. The RCM mechanism improves the general stability of the system by reducing range of motion and velocities in the Cartesian stages when operating in virtual RCM mode, which constrains the tool axis to always intersect the sclerotomy opening on the eye.

Figure 3:
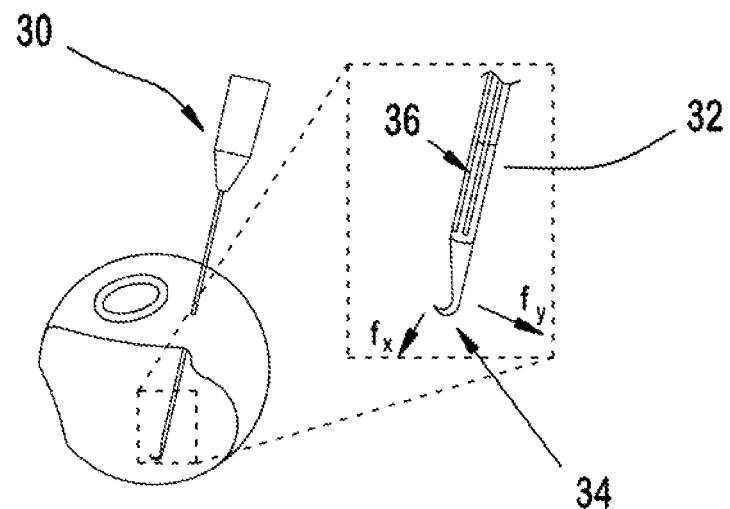
FIG. 3 illustrates an exploded view of an exemplary surgical tool according to the features of the present invention.

With reference to FIG. 3, an exemplary surgical tool 30 to be used in connection with the system and method of the present invention is illustrated. In particular, surgical tool 30 may be specifically designed for use in a cooperative manipulation, such as a system describe above, but may be used in a tele-operative robot as an end effector of a surgical robot. In addition, the surgical tool 30 may be specifically designed for operation on the human eye E.

With continued reference to FIG. 3, the surgical tool 30 includes a tool shaft 32 with a hooked end 34. The surgical tool 30 is manufactured with a force sensor, preferably integrated fiber Bragg grating (FGB) sensors. FBGs are robust optical sensors capable of detecting changes in strain, without interference from electrostatic, electromagnetic or radio frequency sources. Preferably, a number of optical fibers 36 are placed along the tool shaft 32, which allows measuring of the bending of the tool and for calculation of the three in the transverse plane (along $F_x$ and $F_y$) with a sensitivity of 0.25 mN. Accordingly, a sensitive measurement of the forces between the tool and tip can be obtained.

For vitreoretinal microsurgical applications, a three sensor should be chosen that allows for sub-mN accuracy, requiring the sensing of forces that are routinely below 7.5 mN. As such, a very small instrument size is necessary to be inserted through a 25 Ga sclerotomy opening and the force sensor should be designed to be capable of measurements at the instrument's tip, below the sclera.

With reference back to FIGS. 1 and 2, the system 10 includes a processor 26 and a memory device 28. The memory device 28 may include one or more computer readable storage media, as well as machine readable instructions for performing cooperative control of the robot. According to features of the claimed invention, depending upon the forces detected which are sent to the processor 26 (tool-hand forces and/or tool-tip forces), robot velocity is limited by a controller so as to provide a haptic feedback. In particular, a force scaling cooperative control method is used to generate robot response based on the scaled difference between tool-tissue and tool-hand forces.

Figure 4:
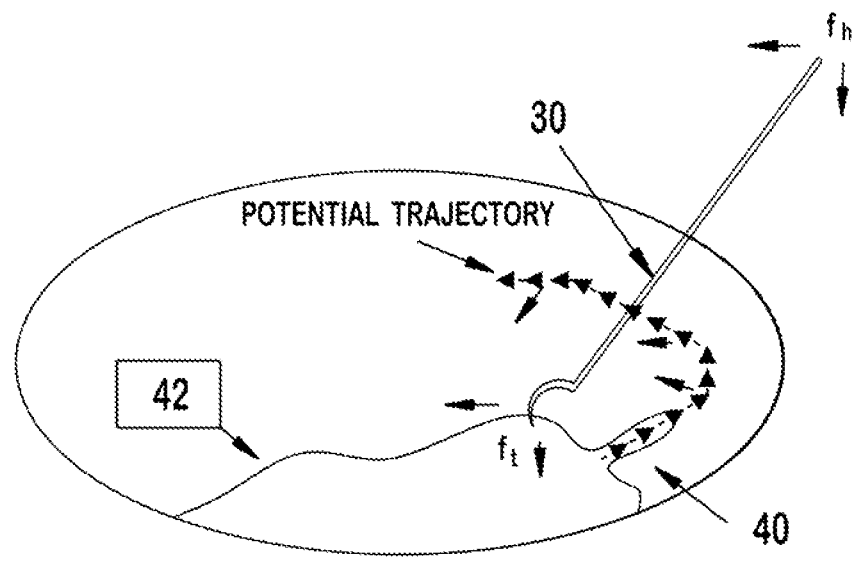
FIG. 4 illustrates a schematic of a peeling process with associated forces.

As discussed above, complications in vitreoretinal surgery may result from excess and/or incorrect application of forces to ocular tissue. As shown in FIG. 4, the surgical tool 30 is used to peel the membrane 42 according to the trajectory shown therein, without generating a tear 40 of the membrane 42. FIG. 4 depicts a peeling process, with associated forces $f_t$ (tool-tip forces) and $f_h$ (user-tool forces). Current practice requires the surgeon to keep operative forces low and safe through slow and steady maneuvering. The surgeon must also rely solely on visual feedback that complicates the problem, as it takes time to detect, assess and the react to the faint cues; a task especially difficult for novice inventors.

According to the features of the present invention, the cooperative control method and system of the present invention uses real-time information to gently guide the operator towards lower forces in a peeling task. The method can be analyzed in two main components, as will be described below.

Safety Limits: The first layer of control enforces a global limit on the forces applied to the tissue at the robot tool tip. Setting a maximum force $f_{max}$, the limiting force $f_{min}$ on each axis would conventionally be defined as $$f_{lim} = f_{max} r_t, \quad r_t = |f_t|/\|f_t\|$$

However, this approach has the disadvantage of halting all motion when the tip force reaches the force limit, i.e., the operator has to back up the robot in order to apply a force in other directions. Distributing the limit with respect to the handle input forces $$f_{lim} = f_{max} r_h, \quad r_h = |f_h|/\|f_h\|$$

gives more freedom to the operator, allowing him/her to explore alternative directions (i.e., search for maneuvers that would generate lower tip forces) even when $f_t$ is at its limit.

Considering the governing law, $$\dot{x} = k_p f_h$$

where $\dot{x}$=velocity.

We apply the limit as follows:

$$\dot{x}_{lim} = \dot{x}\left(\frac{f_{lim} - |f_t|}{l_{lim}}\right)$$

Thus, Cartesian velocity is proportionally scaled with respect to current tip force, where a virtual spring of length $l_{lim}$ is used to ensure stability at the limit boundary.

Active Guidance: The second layer is to guide the operator in order to prevent reaching the limit in the first place. This is achieved by actively biasing, the tool tip motion towards the direction of lower resistance. The ratio $r_t$ is used to update the operator input in the following fashion:

$$\dot{x}_{min} = k_p(1 - r_t s_{min}) f_h$$

where $s_{min}$ is the sensitivity of minimization that sets the ratio of the handle force to be locally minimized. Note that $s_{min} = 0\%$ implies that the operator is not able to override the guided behavior.

Finally, for extra safety, if either sensor is detected as being engaged, e.g., the operator is not applying, any force at the handle (<0.1 N), the robot minimizes $f_t$ by "backing up".

$$\dot{x} = k_p f_t$$

Figure 5:
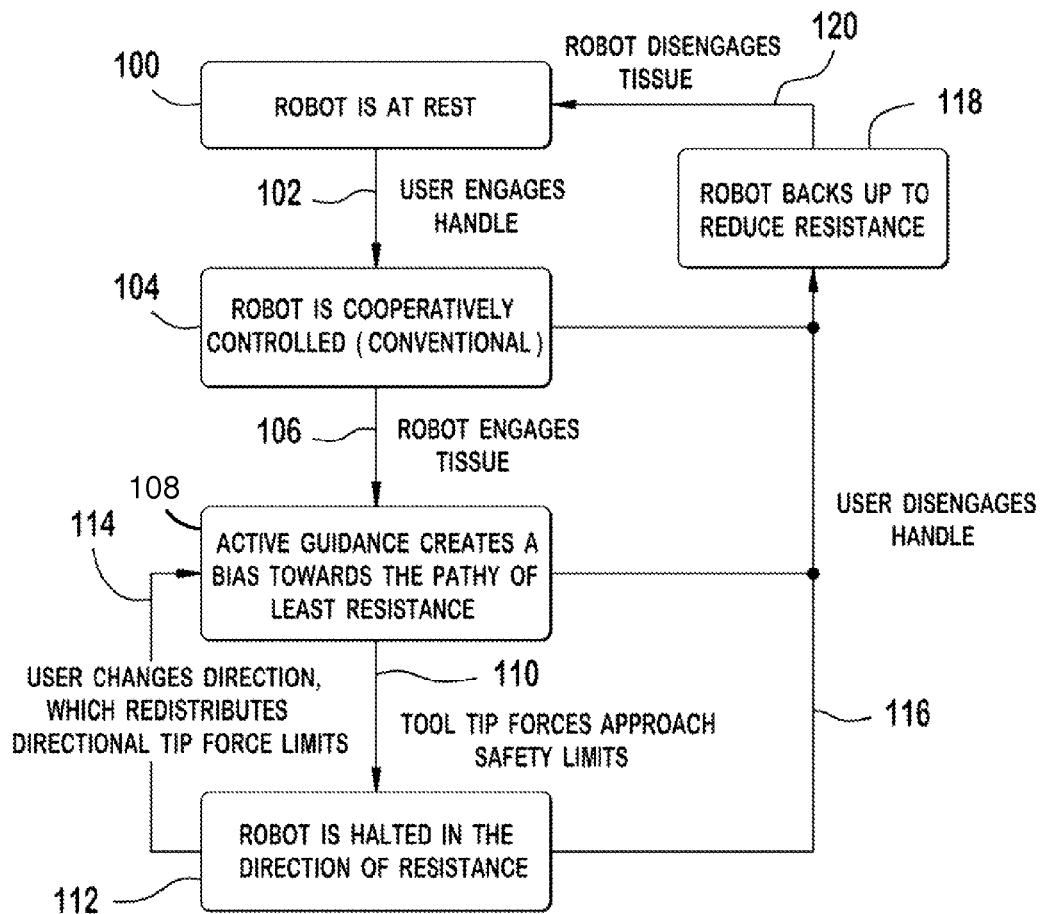
FIG. 5 illustrates a state diagram of how the algorithm works and which state is dominant under which condition according to features of the present invention.

With reference to FIG. 5, a state diagram presents a use-case from the perspective of the user (surgeon), i.e., how the control algorithm behaves and which state is dominant under which conditions. At 100, the robot is at rest. The user then engages the handle at 102. At 104, the robot is cooperatively controlled. At 106, the robot engages tissue. At 108, the robot is actively guided creating a bias towards the path of least resistance. The robot continues this way as the tool tip forces approach the safely limits (110). At 112, the robot is halted in the direction of resistance.

At this point, the user can engage in one of two tasks. First, the user can change direction, which redistributes the direction tip force limits (114). This will then direct the program back, to actively guiding the robot by creating a bias towards the path of least resistance. Second, the user can disengage the handle (116). The robot may then back up to reduce resistance, at 118. At 120, the robot disengages the tissue.

Figure 6:
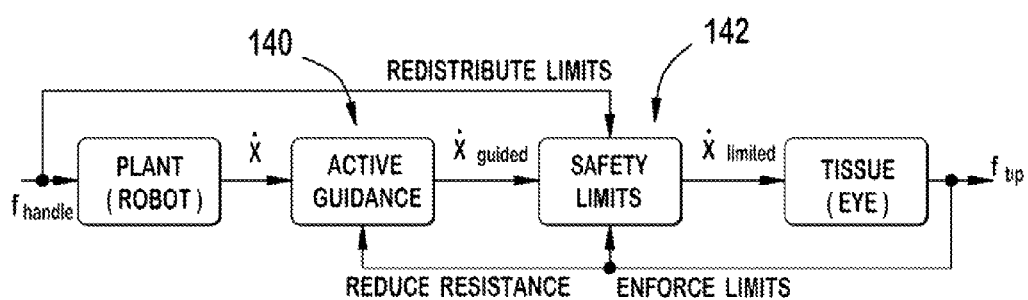
FIG. 6 illustrates a flow diagram of how the algorithm works according to features of the present invention.

With reference to FIG. 6, a simplified control diagram shows the use of the handle and tip forces simultaneously to (1) actively guide the user such that the force exerted on the tissue are minimized; and (2) limit the magnitude of the forces exerted on the tissue, while allowing the user to control the geometric distribution of this limit. As shown in FIG. 6, the data (such as robot velocity or force information) is fed into the two control blocks 140 and 142, in order to modify the control algorithm. That is, the data is sensed and used to manipulate the runtime parameters of the control algorithm, as described by the equations. According to the features of the present invention, the control method and system uses the surgeon's intention (handle forces) and tissue behavior (tip forces) in making a more informed decision.

EXAMPLE

The following Example has been included to provide guidance to one of ordinary skill in the art for practicing representative embodiments of the presently disclosed subject matter. In light of the present disclosure and the general level of skill in the art, those of skill can appreciate that the following Example is intended to be exemplary only and that numerous changes, modifications, and alterations can be employed without departing from the scope of the presently disclosed subject matter. The following Example is offered by way of illustration and not by way of limitation.

Figure 7:
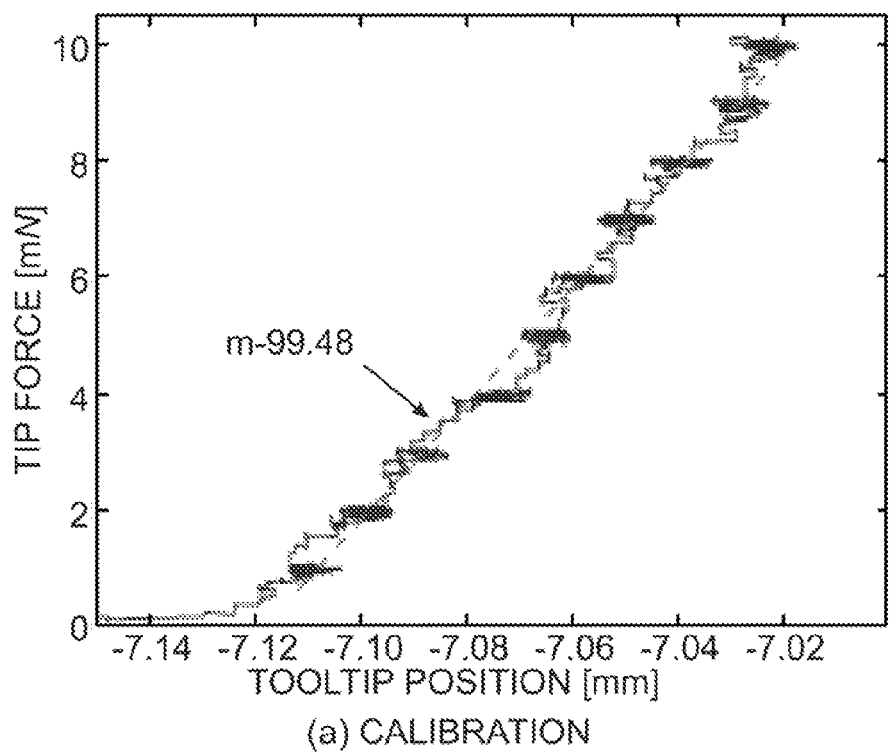
FIGS. 7(a) and 7(b) are graphical representations of force profiles for calibration and membrane peeling according to features of the present invention.
Figure 7:
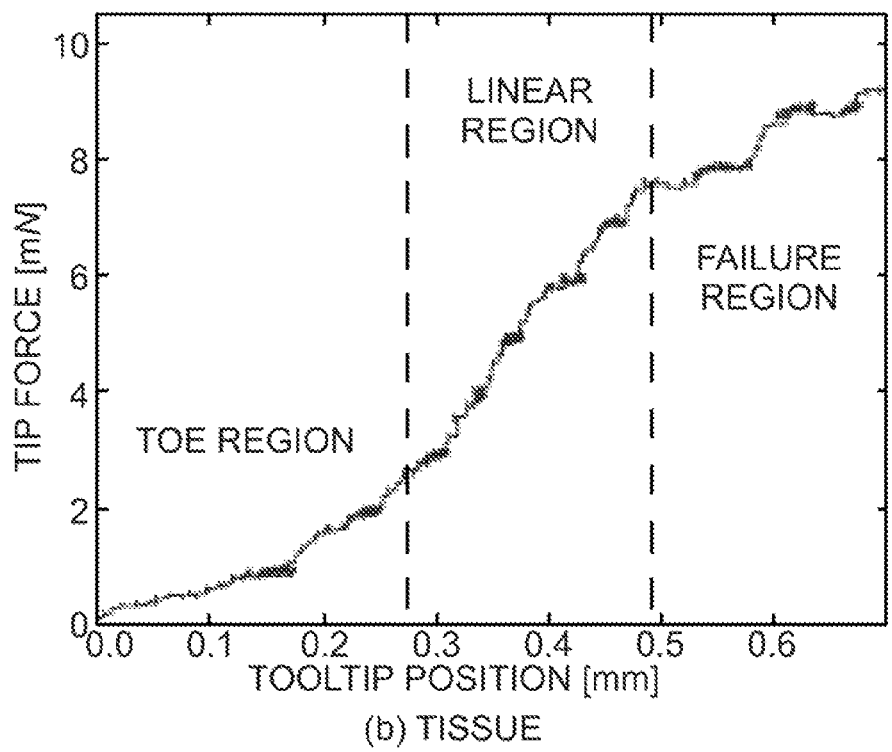

A series of experiments were performed on the inner shell membrane of raw chicken eggs with the aim of identifying and controlling the forces associated with peeling operations. The first set of experiments was carried out to assess the capability of the system in tissue resistance forces through controlled motion and high resolution sensing. Attaching the surgical hook to the sample tissue, a desired constant force was set and the translation was measured with the corrected displacement of the tool tip. The applied force was increased by 1 mN with a 10 s delay between each increment. The system was first tested against a spring, or known stiffness, see FIG. 7(a), where a 2.8% error was observed as compared to the calibrated value. FIG. 7(b) shows a sample force profile for the inner shell membrane. For these trials, the surgical hook was first attached to the intact tissue and force was incrementally applied until failure. The membranes exhibit an average tearing force of 10 mN, after which, continuation of the tear is accomplished with lesser forces (~6 mN).

The characteristic curve obtained reveals a similar pattern to those seen in fibrous tissue tearing. The toe region of the curve, the shape of which is due to recruitment of collagen fibers, is a "safe region" from a surgical point of view and is followed by a predictable linear response. Yielding occurs as bonds begin to break, resulting in a sudden drop on resistive forces due to complete failure. In the surgical setting, this marks the beginning of a membrane being peeled.

In a second set of experiments, the control algorithm was tested. A global limit of 7 mN was set, with a in sensitivity of 90%. An audio cue was also used to inform the operator when the limit was reached. The algorithm was first tested by stripping a piece of tape from a surface. This work revealed the direction of minimum resistance for this phantom. The operator was naturally guided away from the centerline of the tape, following a gradient of force towards a local minimum resistance. Due to mechanical advantage, this corresponded to peeling at ~45° (FIG. 8(a)).

Figure 8:
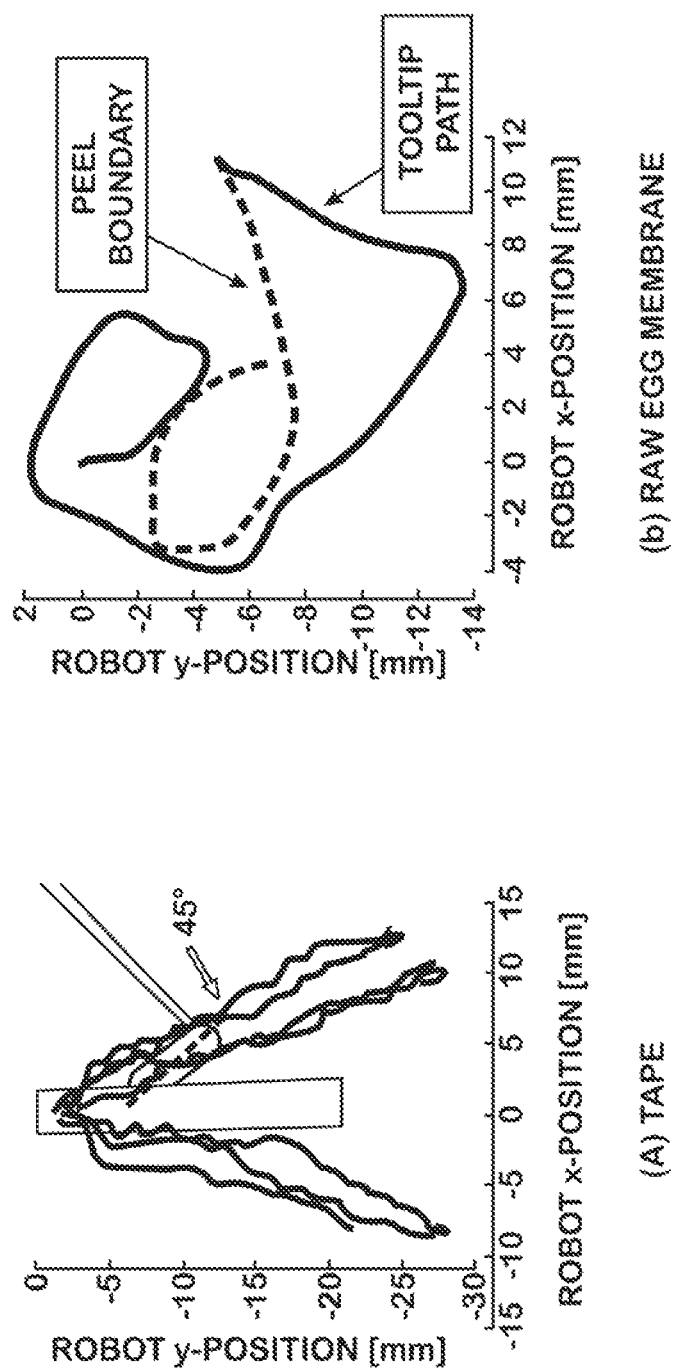
FIGS. 8(a) and 8(b) are resulting trajectories for (a) a simple linear peeling task and (b) peeling task on an egg shell membrane.

Repeating the experiments on the egg membrane, the egg tended to peel in circular trajectories (see FIG. 8(b)). This behavior is consistent with the above trials with the added factor of continuously changing tear direction, i.e., tear follows the ~45° direction of force application. Qualitatively, the algorithm was observed to magnify the perception of tip forces lateral to the operator's desired motion.

Upon reaching the force limit, the operator explored around the boundary in search of points of lower resistance that would enable continuation of peel. This was achieved smoothly without requiring the operator to back up, as the limits of axes were redistributed based on operator's application of handle force.

Accordingly, the present invention advantageously provides for a novel method and system for micro-force guided cooperative control that assists the operator in manipulating tissue in the direction of least resistance, particularly useful in helping surgeons during retinal membrane peeling procedures that require a surgeon to delicately delaminate fragile tissue that is susceptible to hemorrhage and tearing due to undesirable forces. The system and method directs the surgeon to a path of least resistance, instead of requiring the surgeon to back up.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A method of cooperative control of a surgical tool, comprising:
   providing a surgical tool to be manipulated during an operation;
   measuring interaction forces between the surgical tool and tissue of a region of interest;
   measuring interaction forces between a surgeon and a handle of the surgical tool; and
   actively guiding, by a cooperatively controlled robot, the surgical tool by creating a direction-dependent bias in the response of the cooperatively controlled robot to said measured interaction forces between said surgeon and said handle of said surgical tool based on said measured interaction forces between said surgical tool and tissue of said region of interest,
   wherein actively guiding the surgical tool comprises applying a limit on directional tool forces according to $$\dot{x}_{lim} = \dot{x}\left(\frac{f_{lim} - f_t}{l_{lim}}\right),$$

wherein $\dot{x}$ is the velocity, $f_{lim}$ is a limit of the interaction forces between a tip of the surgical tool and the tissue of a region of interest, $f_t$ is the measured interaction forces between the tip of the surgical tool and the tissue of a region of interest, and wherein a virtual spring of length $l_{lim}$ is used to ensure stability at the limit boundary.

2. The method of cooperative control of a surgical tool according to claim 1, wherein directional tool force limits are redistributed when the surgeon changes a direction of the surgical tool.

3. The method of cooperative control of a surgical tool according to claim 1, wherein the limit of the interaction forces between the tip of the surgical tool and the tissue of the region of interest is based on biological data.

4. The method of cooperative control of a surgical tool according to claim 1, wherein the limit of the interaction forces between the tip of the surgical tool and the tissue of the region of interest is based on sensor data gathered during tissue manipulation.

5. The method of cooperative control of a surgical tool according to claim 4, wherein the tissue is eye tissue.

6. The method of cooperative control of a surgical tool according to claim 1, further comprising using the method to perform a blunt tissue dissection.

7. The method of cooperative control of a surgical tool according to claim 1, further comprising dynamically updating virtual fixtures in robot assisted manipulation.

8. A method of cooperative control of a surgical tool, comprising:
   providing a surgical tool to be manipulated during an operation;

measuring interaction forces between the surgical tool and tissue of a region of interest;

measuring interaction forces between a surgeon and a handle of the surgical tool; and actively guiding, by a cooperatively controlled robot, the surgical tool by creating a direction-dependent bias in the response of the cooperatively controlled robot to said measured interaction forces between said surgeon and said handle of said surgical tool based on said measured interaction forces between said surgical tool and tissue of said region of interest, wherein creating a direction-dependent bias comprises enforcing a minimum velocity according to $$\dot{x}_{min} = k_p(1 - r_t s_{min})f_h,$$

where $k_p$ is a gain of the measured interaction forces between the tip of the surgical tool and the tissue of a region of interest; $r_t = |f_t|/\|f_t\|$, where $f_t$ is the measured interaction forces between a tip of the surgical tool and the tissue of a region of interest; $s_{min}$ is a sensitivity of minimization that sets a ratio of the handle force to be locally minimized; and $f_h$ is the measured interaction forces between the surgeon and the handle to the surgical tool.

9. A cooperative control robotic system, comprising:
a tool holder for receiving a surgical tool;
a first sensor for measuring interaction forces between the surgical tool and tissue of a region of interest;
a second sensor for measuring interaction forces between a surgeon and a handle of the surgical tool; and
a cooperatively controlled robot configured to actively guide the surgical tool by creating a direction-dependent bias in a response of said cooperatively controlled robot to said measured interaction forces between said surgeon and said handle of said surgical tool based on said measured interaction forces between said surgical tool and tissue of said region of interest,
wherein the cooperatively controlled robot is configured to actively guide the surgical tool by applying a limit on directional tool forces according to $$\dot{x}_{lim} = \dot{x}\left(\frac{f_{lim} - f_t}{l_{lim}}\right),$$

wherein $\dot{x}$ is the velocity, $f_{lim}$ is a limit of the interaction forces between a tip of the surgical tool and the tissue of a region of interest, $f_t$ is the measured interaction forces between the tip of the surgical tool and the tissue of a region of interest, and wherein a virtual spring of length $l_{lim}$ is used to ensure stability at the limit boundary.

10. The cooperative control robotic system according to claim 9, wherein directional tool force limits are redistributed when the surgeon changes a direction of the surgical tool.

11. The cooperative control robotic system according to claim 9, wherein the limit of the interaction forces between the tip of the surgical tool and the tissue of the region of interest is based on biological data.

12. The cooperative control robotic system according to claim 9, wherein the limit of the interaction forces between the tip of the surgical tool and the tissue of the region of interest is based on sensor data gathered during tissue manipulation.

13. The cooperative control robotic system according to claim 12, wherein the tissue is eye tissue.

14. The cooperative control robotic system according to claim 9, wherein the system is used to perform a blunt tissue dissection.

15. The cooperative control robotic system according to claim 9, wherein the cooperatively controlled robot is configured to dynamically update virtual fixtures in robot assisted manipulation.

16. A cooperative control robotic system, comprising:
a tool holder for receiving a surgical tool;
a first sensor for measuring interaction forces between the surgical tool and tissue of a region of interest;
a second sensor for measuring interaction forces between a surgeon and a handle of the surgical tool; and
a cooperatively controlled robot configured to actively guide the surgical tool by creating a direction-dependent bias in a response of said cooperatively controlled robot to said measured interaction forces between said surgeon and said handle of said surgical tool based on said measured interaction forces between said surgical tool and tissue of said region of interest,
wherein the cooperatively controlled robot is configured to create a direction-dependent bias by enforcing a minimum velocity according to $$\dot{x}_{min} = k_p(1 - r_t s_{min})f_h,$$

where $k_p$ is a gain of the measured interaction forces between the tip of the surgical tool and the tissue of a region of interest; $r_t = |f_t|/\|f_t\|$, where $f_t$ is the measured interaction forces between a tip of the surgical tool and the tissue of a region of interest; $s_{min}$ is a sensitivity of minimization that sets a ratio of the handle force to be locally minimized; and $f_h$ is the measured interaction forces between the surgeon and the handle to the surgical tool.

* * * * *